United States Patent
Tsang

(10) Patent No.: US 9,278,153 B1
(45) Date of Patent: Mar. 8, 2016

(54) PESTICIDE-FREE AGRICULTURAL AIR STERILIZATION AND FARMING EQUIPMENT

(71) Applicant: Chun Hung Tsang, Ma On Shan (HK)

(72) Inventor: Chun Hung Tsang, Ma On Shan (HK)

(*) Notice: Subject to any disclaimer, the term of this patent is extended or adjusted under 35 U.S.C. 154(b) by 0 days.

(21) Appl. No.: 14/673,680

(22) Filed: Mar. 30, 2015

(51) Int. Cl.
    *A61L 9/22* (2006.01)
    *A61L 9/12* (2006.01)
    *A01M 1/22* (2006.01)
    *A01M 23/38* (2006.01)
    *A01M 29/24* (2011.01)

(52) U.S. Cl.
    CPC *A61L 9/12* (2013.01); *A01M 1/223* (2013.01); *A01M 23/38* (2013.01); *A01M 29/24* (2013.01)

(58) Field of Classification Search
    CPC .............................. A61L 9/12; A01M 7/0003
    USPC ....................................................... 422/123
    See application file for complete search history.

(56) References Cited

U.S. PATENT DOCUMENTS

| 6,279,589 | B1* | 8/2001 | Goodley | B08B 9/0936 134/102.1 |
| 6,510,859 | B1* | 1/2003 | Kamikawa | B08B 3/102 134/100.1 |
| 7,022,225 | B1* | 4/2006 | Clawson | B01D 19/0063 210/188 |
| 2003/0173276 | A1* | 9/2003 | Arnaud | B01D 21/2433 210/143 |
| 2009/0233839 | A1* | 9/2009 | Lynn | A61L 2/183 510/370 |

* cited by examiner

*Primary Examiner* — Kevin Joyner
*Assistant Examiner* — Holly Mull

(57) ABSTRACT

Methods and devices are provided for an agricultural pesticide-free air sterilization machine. In one embodiment, the machine employs a liquid-gas mixing device, an ozone generator, a water inlet; and/or a water outlet. The mixing device may have a water inlet, a water outlet, a feed pump, a jet device, and/or a liquid-gas mixer. Further, the ozone generator utilizes an oxygen generator, an oxygen storage container, and a high voltage discharge chamber. In other embodiments, the feed pump is connected to the water inlet of the jet device via a hose, and the ozone generator is connected to the gas inlet of the jet device via a gas tube.

7 Claims, 5 Drawing Sheets

PESTICIDE-FREE AGRICULTURAL AIR STERILIZATION AND FARMING EQUIPMENT

FIELD OF THE INVENTION

The present invention relates to farming equipment, and more particularly to a pesticide-free air sterilization machine and a comprehensive agricultural pesticide-free farming equipment.

BACKGROUND OF THE INVENTION

Figure 5:
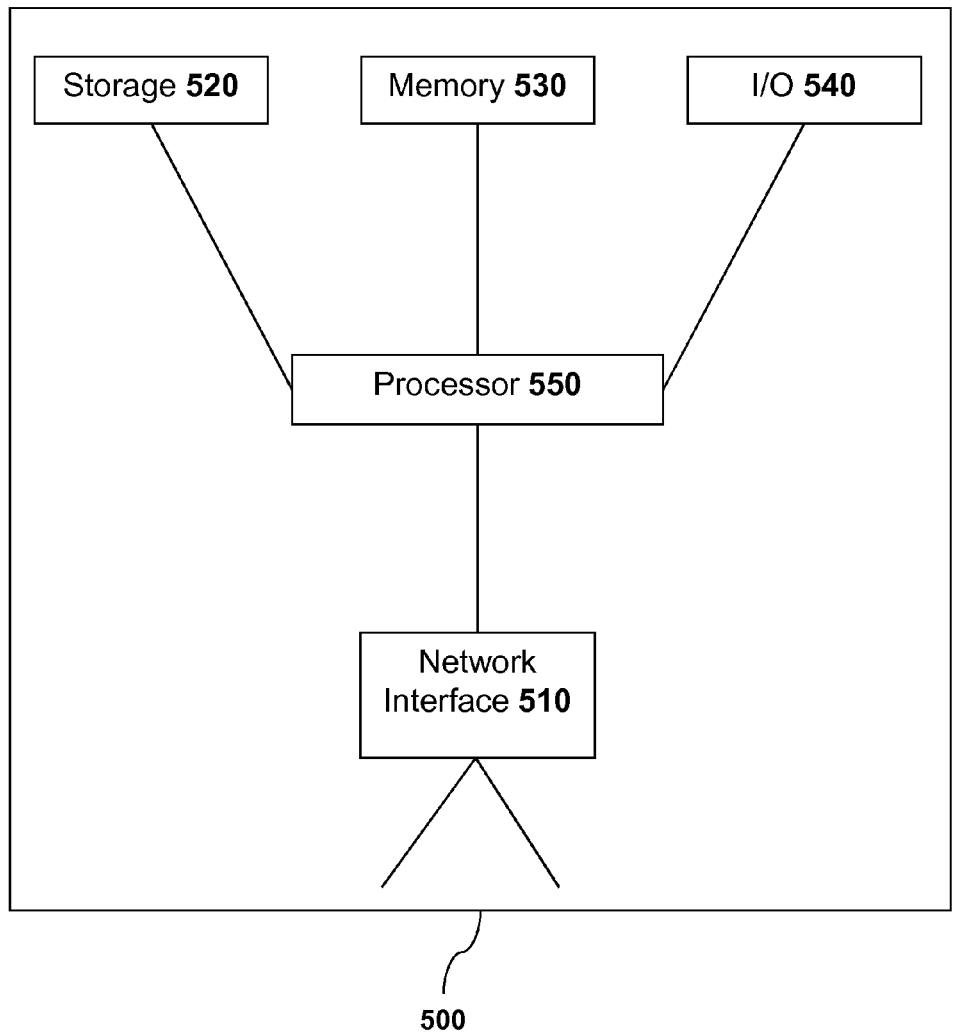

Current agricultural methods require protection of crops in order to facilitate normal growth without haze bacteria, powdery mildew, anthrax bacteria mole crickets, brown spot fungus, downy mildew, canker bacteria, viruses and other types of fungi infection. At present, there exists both traditional agricultural pesticide methods and pesticide-free methods. The pesticide-free methods include the use of ultraviolet disinfection, ozone disinfection, and other similar methods. It is well known that pesticides provide effective sterilization, but the chemical composition of such treatments is likely to result in residues that cause crop pollution and other side effects. Such side effects are prone to entering the food chain and affecting the health of consumers. Therefore non-pesticide sterilization is now the mainstream trend.

Ozone sterilization is also a popular method used in the agriculture and aquaculture industries. Ozone sterilization is safe, non-toxic, and results in no residue contamination. It is generally recognized as an effective sterilization method, and is less burdensome and costly to apply when compared to ultraviolet disinfection. One disadvantage of ozone sterilization is limited application range. It is difficult to apply ozone sterilization to a wide area of arable land. In order to achieve a comprehensive and effective sterilization and disinfection, doing so would result in a more complex technical application method, and a higher cost of materials and labor.

In addition to the need for sterilization of farming, there is also the requirement for pest control. Both sterilization and pest control are needed in order to protect the healthy growth of crops. Therefore, pest control and sterilization must be carried out side by side to fully promote agricultural planting harvest, and to guarantee return. Therefore, there is an unfulfilled need in the art to produce a crop sterilization method that enables a broad spectrum application to a relatively large crop area.

SUMMARY OF THE INVENTION

Systems, apparatuses and/or methods are directed to a non-polluting, highly efficient, pesticide-free agricultural air sterilization machine, as well as comprehensive pesticide-free farming equipment for total protection of crops to ensure better crop growth and more fruitful harvests. The pesticide-free air sterilization machine may have an ozone generator and a water vapor mixing device. The ozone generator may use gas pipes to connect the generator with the mixing device. The mixing device has an attached inlet for water to enter, and also has an attached outlet for water to exit.

Furthermore, the water vapor mixing device may employ a feed pump, a jet device, and/or a water vapor mixer. The feed pump is connected to water inlet of the jet device via a pipeline. The jet device may have a gas inlet that is connected to the ozone generator via a gas pipe. The jet device may have a water outlet that is connected with the water vapor mixer. The water inlet of the feed pump also serves as a water inlet to the water vapor mixing device, whereas the water outlet of the jet device serves as a water outlet for the water vapor mixing device.

Further, the ozone generator may have an oxygen generator, an oxygen storage container, and/or a high-voltage discharge chamber. The oxygen generator is connected via a gas tube to the oxygen storage container. The storage container connects to the high voltage discharge chamber, and in turn the high voltage discharge chamber connects via a gas tube to the gas inlet of the jet device.

In further embodiments, the oxygen storage container may have two high voltage discharge chambers. The two high voltage discharge chambers connect in parallel to the jet device.

Further, a chassis is fitted with electronic high voltage circuit, where the high voltage circuit electrically connects to the high voltage discharge chambers.

Further, a sterilization device is installed in the chassis. The chassis may be provided with a water inlet and a water storage tank. The water vapor mixing device has a water inlet that is connected to the water inlet of the chassis, and the water vapor mixing device has a water outlet that connects with the water storage tank.

Further, the chassis may also have a motor, a high-pressure pump, and/or a hose reel disk. The motor connects to the high-pressure pump. A water hose is used to couple the high pressure pump to a water storage tank. A hose is also coupled to a spray gun attached to the hose reel disk. The bottom of the chassis may be fitted with casters. The water storage tank may also have a discharge pipe. A switch valve may be installed along the pipe as well.

Application of the above agricultural pesticide-free air sterilization machine is to be carried out contemporarily or in close succession with a pest control device application. The pest control device application may also include a housing, a trap lamp, and high-voltage grid.

The pest control device may also be provided with solar panels. The solar panels are connected with rechargeable batteries to supply electric power to the trap lamp and the high-voltage grid.

The disclosed technology advantageously uses ozone water for disinfection and sterilization, without applying any chemical residue to crops which may result in pollution. The disclosed technology ensures the pH of crops is restored to healthy levels. The machine has a highly efficient ozone water output. Further the machine has a simple structure that is flexible and maneuverable. Implementation of a wide range of agricultural land sterilization may be effectively carried out thereby reducing the cost of cultivation and labor consumption, and ensuring a healthy farming harvest, and improved agricultural yields.

A better understanding of the disclosed technology will be obtained from the following brief description of drawings illustrating exemplary embodiments of the disclosed technology.

BRIEF DESCRIPTION OF THE DRAWINGS

FIG. 1 illustrates an architecture block diagram of an agricultural pesticide-free air sterilization machine.

FIG. 2 shows a schematic diagram of a chassis of an agricultural pesticide-free air sterilization machine.

FIG. 3 shows a schematic diagram from a different angle of a chassis of an agricultural pesticide-free air sterilization machine.

FIG. 4 shows a perspective elevation view of a pest control device.

FIG. 5 is a high-level block diagram of a microprocessor device that may be used to carry out the disclosed technology.

A better understanding of the disclosed technology will be obtained from the following detailed description of embodiments of the disclosed technology, taken in conjunction with the drawings.

DETAILED DESCRIPTION

References will now be made in detail to the present exemplary embodiments, examples of which are illustrated in the accompanying drawings. Whenever possible, the same reference numbers will be used throughout the drawings to refer to the same or like parts.

Referring now to the figures, an agricultural pesticide-free air sterilization machine is provided. In one embodiment, the machine employs a liquid-gas mixing device, an ozone generator, a water inlet; and/or a water outlet. The mixing device may have a water inlet, a water outlet, a feed pump, a jet device, and/or a liquid-gas mixer. Further, the ozone generator utilizes an oxygen generator, an oxygen storage container, and a high voltage discharge chamber. In other embodiments, the feed pump is connected to the water inlet of the jet device via a hose, and the ozone generator is connected to the gas inlet of the jet device via a gas tube.

Figure 1:
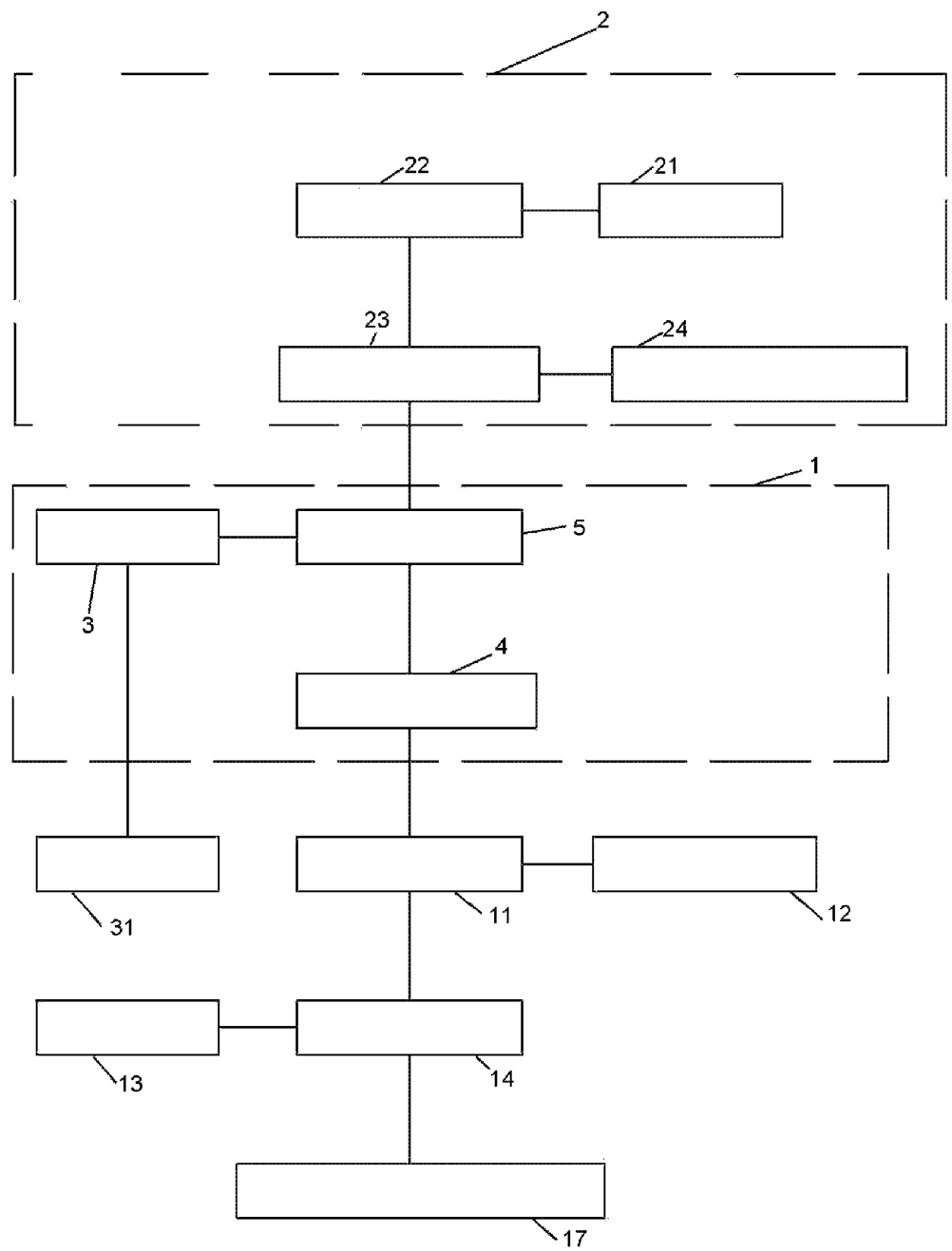

FIG. 1 illustrates an architecture block diagram of an agricultural pesticide-free air sterilization machine. Depicted in FIG. 1 are an ozone generator 2 and a water vapor mixing device 1. The ozone generator 2 uses a gas tube to connect to the water vapor mixing device 1. The water vapor mixing device 1 has a water inlet and a water outlet. Tap water enters from the inlet into the water vapor mixing device 1. The water is mixed with ozone gas generated by the ozone generator. The ozone gas enters into the water vapor mixing device to mix with water in order to combine into ozone water. The ozone water outputted from the water outlet may be used for agriculture farming purposes, directed through irrigation pipes for sterilization, or used for spray sterilization. When ozone water is sprayed into the air, it can also adjust local environmental pH back to an appropriate level to protect environmental health.

The water vapor mixing device 1 may have a feed pump 3, a jet device 5, and a water and gas mixer 4. Specifically, a pipeline connects the feed pump with a water inlet of the jet device. A gas tube connects a gas inlet attached to the jet device to the ozone generator. The water outlet connects to the water vapor mixing device. The water inlet of the feed pump serves to inject water into the water vapor mixing device. The water outlet of the water vapor mixer 4 serves as the water outlet of the water vapor mixing device. The feed pump takes tap water, pressurizes it, and injects it into the jet device 5. At the same time, the ozone generator generates ozone gas to be inputted into the jet device 5. The ozone gas and water pass through the jet device to enter the water vapor mixer and combine into ozone water.

More specifically, the ozone generator includes an oxygen generator 21, an oxygen storage container 22, and a high voltage discharge chamber 22. The oxygen generator 21 connects to the oxygen storage container 22 via a gas tube. The oxygen generator 21 produces a large volume of oxygen continuously to input into the oxygen storage container 22 in order to maintain sufficient oxygen supply. The oxygen storage container is connected to the high voltage discharge chamber 23, where the chamber connects to the gas inlet of the jet device 5 via a gas pipe. The high voltage discharge chamber 23' produces highly concentrated ozone efficiently and at a low cost.

In an embodiment, two high voltage discharge chambers 23 are connected in parallel to the oxygen storage container 22. The two chambers 23 are connected in parallel to the jet device 5. The oxygen generator 21 inputs sufficient oxygen-enriched air into the oxygen storage container 22, and then the two high voltage discharge chambers further increase the efficiency of the ozone production. The jet device inputs a large volume of ozone to increase the concentration of the ozone water. At the same time the jet device lowers the diffusion rate of ozone molecules thereby resulting in more effective sterilization.

Figure 2:
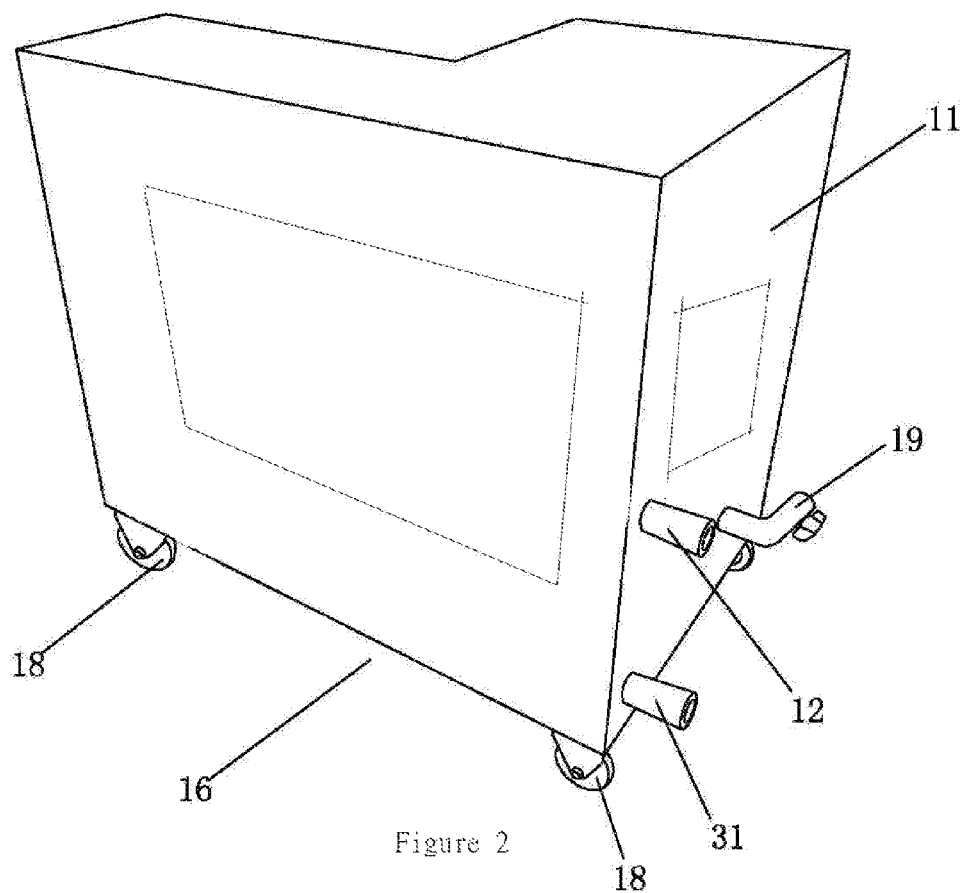

Furthermore, the ozone generator 2 is fitted with an electronic high voltage circuit 24, where the circuit 24 electrically connects to the high voltage discharge chamber 23. The circuit 24 converts ordinary a public electricity supply into the voltage power required by the high voltage discharge chambers 23, without using any additional transformers, thereby integrating circuit control and corresponding equipment, resulting in a single point of convenient operation FIG. 2 shows a schematic diagram of a chassis of an agricultural pesticide-free air sterilization machine. the sterilizing machine is mounted within a chassis 16. The chassis 16 is fitted with inlet pipe 31 and the water storage tank 11. The water inlet of the water vapor mixing device 1 connects to the water inlet of the inlet pipe, where the water outlet of the water vapor mixing device 1 connects to the water storage tank 11. The tank has a water outlet pipe 12. To use for application, the inlet pipe 31 is connected to tap water source, and the water outlet is connected to irrigation pipes, which is convenient to use on farm lands.

Figure 3:
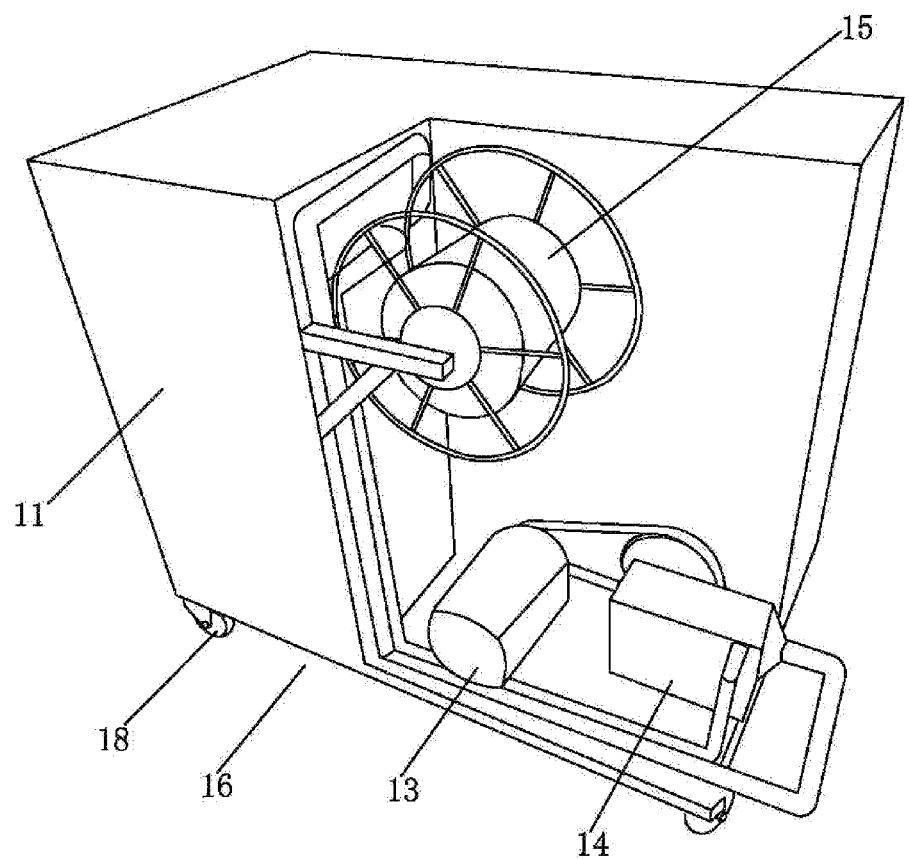

FIG. 3 shows a schematic diagram from a different angle of a chassis of an agricultural pesticide-free air sterilization machine. Depicted in this Figure is the chassis 16 which has a motor 13, a high-pressure pump 14, and a reel plate 15. The drive motor 13 is connected to the high pressure pump 14. The high pressure pump 14 is coupled, via the pipes, to the storage tank(s) 11. The pump 14 is also coupled via the hose to the spray gun 17, and the hose is coiled onto the reel plate 15. Sterilization is carried out using the hose and spray gun 17. In addition, the retractable hose allows workers to use the sterilization machine as a center for a wide range of spray, thus avoiding the spraying limitation encountered when using a jug, resulting in more effectively implemented sterilization, convenience and efficiency.

Further, as shown in FIG. 2 and FIG. 3, the bottom of the chassis 16 is provided with casters 18, so that the sterilization machine is easy to maneuver requiring minimal manpower. Further, the chassis 16 can be transferred easily onto a vehicle so that the sterilization machine can easily be transported across a large area of agricultural land, achieving greater coverage and cost efficiency. The storage tank 11 is also provided with a discharge pipe 19. The discharge pipe 19 has a switch valve installed, which is used when the work is completed in order to empty water out of tank 11, to avoid stagnant water being stored for too long.

In order to carry out sterilization on agricultural land, ozone water can be applied by using an irrigation method or by spraying. Whether irrigation or spraying is used may be dependent on the type of crops. Irrigation is carried out by connecting the water outlet of the machine to watering pipes on farmland. An alternative method may be to use the ozone water independently without any devices. Further, the machine is equipped with a hose and a spray gun 17 to facilitate spray sterilization. In addition, the machine may be connected to an ordinary public power supply or a power generator in order to promote greater versatility. Additionally, ozone water is also capable of adjusting the local pH of soil and air, which helps to restore favorable conditions for planting and farming.

Figure 4:
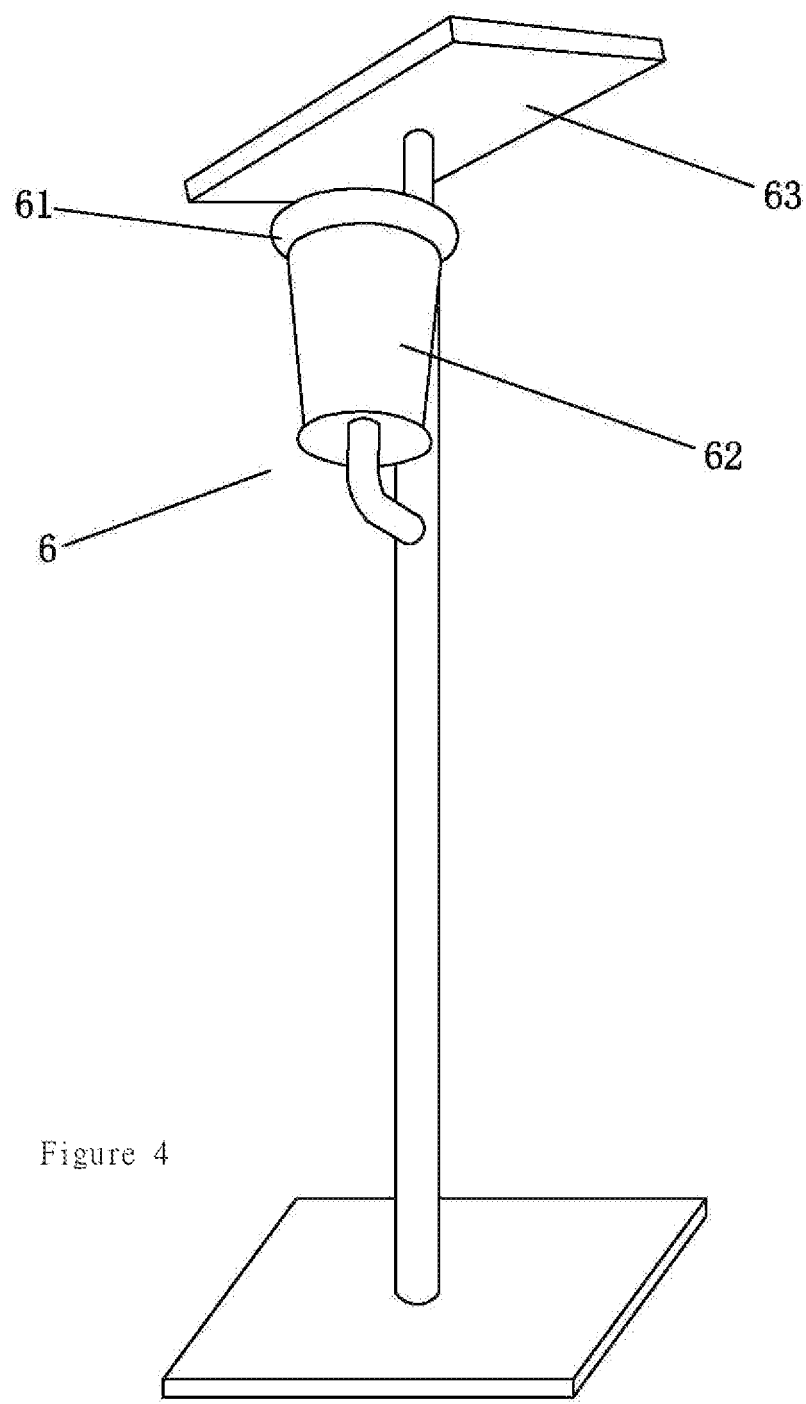

FIG. 4 shows a perspective elevation view of a pest control device. The application of the air sterilization machine described in FIGS. 1 through 3 in combination with the pest control device 6 of FIG. 4 results in a comprehensive solution. The pest control device 6 has a housing 61. The housing 61 is provided with a trap lamp and a high-voltage grid 62. Pests in agricultural land within range of the device 6 are attracted and neutralized by the trap lamp and the high-voltage grid 62. The combination of using the air sterilization machine and the pest control device 6 provides a complete protective solution for crops in avoiding pest infestation and bacteria infection. Thus, this solution ensures high-quality and high-yield farming without pesticide pollution as well as the environmental and health side effects that go with it.

Even further, the pest control device 6 is also provided with solar panels 63. The solar panels 63 are connected with rechargeable batteries, which connect to the trap lamp and the high voltage grid 62 (not shown). The panels convert solar energy into electrical energy and to store for powering the pest control device 6. This also has a positive environmental affect by reducing power consumption and environmental health.

FIG. 5 is a high-level block diagram of a microprocessor device that may be used to carry out the disclosed technology. The device 500 may be employed to partially or wholly automate certain functions and components of the disclosed technology. The device 500 comprises a processor 550 that controls the overall operation of a computer by executing the system's program instructions which define such operation. The system's program instructions may be stored in a storage device 520 (e.g., magnetic disk, database) and loaded into memory 530 when execution of the console's program instructions is desired. Thus, the device 500 will be defined by the program instructions stored in memory 530 and/or storage 520, and the console will be controlled by processor 550 executing the console's program instructions.

The device 500 may also include one or a plurality of input network interfaces for communicating with other devices via a network (e.g., the internet). The device 500 further includes an electrical input interface for receiving power and data. The device 500 also includes one or more output network interfaces 510 for communicating with other devices. The device 500 may also include input/output 540 representing devices which allow for user interaction with a computer (e.g., display, keyboard, mouse, speakers, buttons, etc.).

One skilled in the art will recognize that an implementation of an actual device will contain other components as well, and that FIG. 5 is a high level representation of some of the components of such a device for illustrative purposes. It should also be understood by one skilled in the art that the method and devices depicted in FIGS. 1 through 4 may be implemented, in whole or in part, on a device such as is shown in FIG. 5.

While it is obvious that modification or proper change and combination can be made to the present system according to the present invention by those skilled in the art, however, without departing from the contents, spirit and scope of the invention, any variations that are intended to achieve the techniques disclosed in the present invention should be within the scope of this invention. Specifically, it should be pointed out that all similar substitutions and modifications are obvious to those skilled in the art, and they are deemed to be within the scope and content of the present invention.

It is to be understood that the foregoing detailed description and accompanying drawings relate to a preferred illustrative embodiment of the invention. However, various changes and modifications may be made without departing from the spirit and scope of the invention. Accordingly, the present invention is not limited to the specific arrangements as shown in the drawings and described in detail herein above. The exemplary materials, constructions and illustrations included in the preferred embodiment and this patent application should therefore not be construed to limit the scope of the present invention, which is defined by the appended claims.

While the disclosed invention has been taught with specific reference to the above embodiments, a person having ordinary skill in the art will recognize that changes may be made in form and detail without departing from the spirit and the scope of the invention. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the invention.

The invention claimed is:

1. An agricultural pesticide-free air sterilization machine, the machine comprising:
    a. a liquid-gas mixing device, wherein the mixing device further comprises:
        i. a water inlet;
        ii. a water outlet;
        iii. a feed pump;
        iv. a jet device, wherein the jet device has a water inlet, a water outlet, and a gas inlet; and
        v. a liquid-gas mixer;
    b. an ozone generator, wherein the ozone generator further comprises:
        i. an oxygen generator;
        ii. an oxygen storage container; and
        iii. a first high voltage discharge chamber;
    c. a water inlet;
    d. a water outlet; and
    e. a pest control device, wherein:
    the feed pump is connected to the water inlet of the jet device via a first hose;
    the ozone generator is connected to the gas inlet of the jet device via a first gas tube;
    the liquid-gas mixer is connected to the water outlet of the jet device via a second hose;
    the water inlet of the feed pump is connected to the water inlet of the liquid-gas mixing device via a third hose;
    the water outlet of the liquid-gas mixer is connected to the water outlet of the liquid-gas mixing device via a fourth hose;
    the oxygen generator is connected to the oxygen storage container via a second gas tube;
    the oxygen storage container is electrically connected to the first high voltage discharge chamber;
    the first high voltage discharge chamber is connected to the gas inlet of the jet device via a third gas tube; and
    the pest control device has:
        at least one rechargeable battery;
        a solar panel electrically connected to the at least one rechargeable battery;
        a trap lamp electrically connected to the at least one rechargeable battery; and
        a high-voltage grid electrically connected to the at least one rechargeable battery.

2. The agricultural pesticide-free air sterilization machine of claim 1, further comprising a second high-voltage discharge chamber wherein the first high-voltage discharge chamber and the second high-voltage chamber are connected in parallel with the oxygen storage container and the jet device.

3. The agricultural pesticide-free air sterilization machine of claim 1, wherein the ozone generator is connected to the first high voltage discharge chamber via a high-voltage circuit.

4. The agricultural pesticide-free air sterilization machine of claim 1, further comprising:
   a chassis having a chassis water inlet and a chassis water storage tank, wherein the water inlet of the machine is connected to the chassis water inlet and the water outlet of the machine is connected to the water outlet of the water storage tank.

5. The agricultural pesticide-free air sterilization machine of claim 4, further comprising:
   a high voltage pump connected to the water storage tank via a fifth hose;
   a motor coupled to the high voltage pump to provide power;
   a reel disc;
   a hose coiled around the reel disc; and
   a spray gun attached to the hose coiled around the reel disc.

6. The agricultural pesticide-free air sterilization machine of claim 5, wherein the chassis has casters at a bottom thereof, and the water storage tank is further provided with a discharge pipe, wherein the discharge pipe is installed with a switch valve.

7. The agricultural pesticide-free air sterilization machine of claim 1, wherein:
   the machine applies ozone water to carry out sterilization.

* * * * *